United States Patent [19]

Tvrtkovic-Sahin et al.

[11] Patent Number: Plant 7,400

[45] Date of Patent: Dec. 18, 1990

[54] ASTER PLANT NAMED ROSE BUTTERFLY

[76] Inventors: Zelimir K. Tvrtkovic-Sahin, Barnsteenstraat 24, 2403 BZ, Alphen aan den Rijn; Petrus J. Akerboom, Paradijsweg 61, 2461 TL, Ter Aar, both of Netherlands

[21] Appl. No.: 378,305

[22] Filed: Jul. 11, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

An Aster plant named Rose Butterfly particularly characterized by its cupped capitulum form; daisy capitulum type; red-purple ray floret color; diameter across face of capitulum of 25 to 27 mm at maturity; strong, well branched flower stems; and many capitula per inflorescence on short pedicels.

1 Drawing Sheet

The present invention comprises a new and distinct cultivar of Aster plant, hereinafter referred to by the cultivar name Rose Butterfly.

Rose Butterfly is a product of a planned breeding program which had the objective of creating new perennial Aster cultivars for year-round commercial production and having well branched flower stems, good flower size, rose flower color, good flower form, and long lasting quality of the cut flowers. Such traits in combination were not present in previously available commercial cultivars.

Rose Butterfly was originated from a hybridization made by the inventors K. Sahin and P. Akerboom in a controlled breeding program in Ter Aar, the Netherlands, in 1984. The female parent of Rose Butterfly was *Aster pringlei* c.v. Monte Casino. The male parent was an unnamed *Aster novi-belgii* seedling.

Rose Butterfly was discovered and selected as one flowering plant within the progeny of the stated parentage by the inventors K. Sahin and P. Akerboom on Sept. 2, 1985 in a controlled environment in Ter Aar, and identified as Seedling No. 84/130.

The first act of asexual reproduction of Rose Butterfly was accomplished when vegetative cuttings were taken from the initial selection in November of 1985 in a controlled environment in Ter Aar, by a technician working under formulations established and supervised by K. Sahin and P. Akerboom.

Horticultural examination of selected units initiated in 1985 and 1986 has demonstrated that the unique combination of characteristics as herein disclosed for Rose Butterfly are firmly fixed and are retained through successive generations of asexual reproduction.

Rose Butterfly has not been observed under all possible environmental conditions. The phenotype may vary significantly with variations in environment such as temperature, light intensity and daylength.

The following observations, measurements and comparisons describe plants grown in Ter Aar under greenhouse conditions which approximate those generally used in commercial greenhouse practice in The Netherlands.

The following traits have been repeatedly observed and are determined to be basic characteristics of Rose Butterfly, which, in combination, distinguish this Aster as a new and distinct cultivar:

1. Cupped capitulum form.
2. Daisy capitulum type.
3. Red-purple ray floret color.
4. Diameter across face of capitulum of 25 to 27 mm at maturity.
5. Strong, well branched flower stems.
6. Many capitula per inflorescence on short pedicels.

The accompanying photographic drawing shows typical inflorescence of Rose Butterfly, with the colors being as nearly true as possible with illustrations of this type. The color photograph is a front perspective view of Rose Butterfly grown as a single stem cut spray Aster.

Of the commercial cultivars known to the inventors, the most similar in comparison to Rose Butterfly is the female parent Monte Casino. Reference is made to attached Chart A, which compares certain characteristics of Rose Butterfly to the same characteristics of Monte Casino.

In comparison to Monte Casino, Rose Butterfly has thicker and greener leaves, stronger flower stems, better branching, more capitula per inflorescence, larger flowers and better lasting quality of the cut flowers. With regard to the last mentioned characteristic, when grown under similar conditions, the blossoms of Rose Butterfly will last 2–3 days longer than the flowers of Monte Casino. In addition, the ray floret color of Rose Butterfly is red-purple, while the ray floret color of Monte Casino is white. Similar traits are capitulum form and type, spray formation and photoperiodic light reaction.

In the following description color references are made to The Royal Horticultural Society Colour Chart. The color values were determined between 12:00 and 14:00 hours on Mar. 16, 1987 at Alphen aan den Rijn, The Netherlands.

Classification:

*Botanical.*—*Aster pringlei* × *novi-belgii* cv Rose Butterfly.

*Commercial.*—Small daisy-like spray Aster perennial.

INFLORESCENCE

A. Capitulum:

*Form.*—Cupped.

*Type.*—Daisy.
*Diameter across face.*—25-27 mm.
*Arrangement.*—Raceme inflorescence.

B. Corolla of ray florets:
*Color (general tonality from a distance of three meters).*—Red-purple.
*Color (upper surface).*—Closest to 62B.
*Color (under surface).*—Closest to 62C.
*Shape of floret.*—Narrow, oblong, straight.
*Size of floret.*—11 mm long×1 mm wide.
*Number of ray florets.*—28-31.

C. Corolla of disc florets:
*Color (mature).*—Closest to 1C to 1D.
*Color (immature).*—Closest to 1C to 1D.
*Diameter of disc.*—8-9 mm.

D. Reproductive organs:
*Androecium.*—Present on disc florets only; no pollen.
*Gynoecium.*—Present on both ray and disc florets.

PLANT

A. General appearance:
*Height.*—Medium to tall; depends on light conditions. Under continuous long days plant can grow up to 2 meters tall heavy branching.

B. Foliage:
*Color.*—137A.
*Shape.*—Oblanceolate and linear, with occasional downward reflexing at the tip.
*Length.*—Medium to long, width medium.
*Margin.*—Entire.
*Arrangement.*—Alternate, with angle acute.

CHART A
COMPARISON OF ROSE BUTTERFLY AND MONTE CASINO

| | Rose Butterfly | Monte Casino |
|---|---|---|
| Ray Floret Color | Red-purple | White |
| Capitulum Form and Type | Cupped daisy | Cupped daisy |
| Spray formation | Compound | Compound |
| Pedicels | 5-15 mm long | 7 mm long |
| Diameter across face of capitulum | 25-27 mm | 20-22 mm |
| Number of ray florets | 28-31 | 27 |

Comparisons made on plants grown as single stem spray Asters in Ter Aar, The Netherlands

We claim:

1. A new and distinct Aster plant named Rose Butterfly, as described and illustrated.

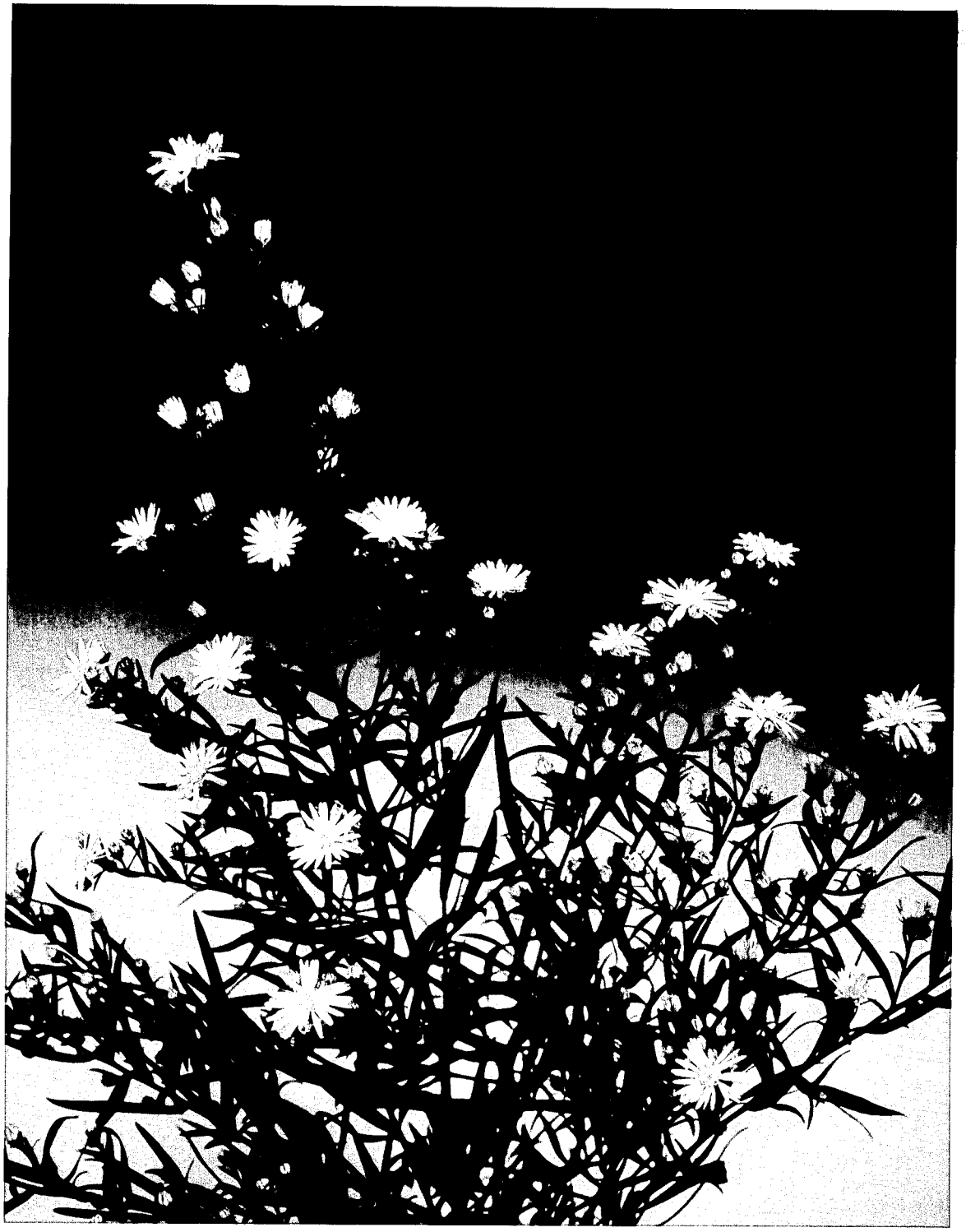

* * * * *